(12) United States Patent
Eaton

(10) Patent No.: US 12,134,471 B2
(45) Date of Patent: Nov. 5, 2024

(54) METHODS AND SYSTEMS FOR DRONE BASED ASSISTANCE

(71) Applicant: DISH Network L.L.C., Englewood, CO (US)

(72) Inventor: Zane C. Eaton, Pompano Beach, FL (US)

(73) Assignee: DISH Network L.L.C., Englewood, CO (US)

(*) Notice: Subject to any disclaimer, the term of this patent is extended or adjusted under 35 U.S.C. 154(b) by 411 days.

(21) Appl. No.: 17/545,602

(22) Filed: Dec. 8, 2021

(65) Prior Publication Data
US 2023/0174234 A1 Jun. 8, 2023

(51) Int. Cl.
*B64C 39/02* (2023.01)
*B64D 45/00* (2006.01)
*G05D 1/00* (2006.01)
*G06F 3/01* (2006.01)
*G06N 20/00* (2019.01)
(Continued)

(52) U.S. Cl.
CPC .......... *B64C 39/024* (2013.01); *B64D 45/00* (2013.01); *G05D 1/12* (2013.01); *G06F 3/017* (2013.01); *G06N 20/00* (2019.01); *G16H 40/63* (2018.01); *B64U 2101/00* (2023.01)

(58) Field of Classification Search
CPC ...... B64C 39/024; G16H 40/63; G06N 20/00; B64D 45/00; G05D 1/12; G06F 3/017; B64U 2101/00
See application file for complete search history.

(56) References Cited

U.S. PATENT DOCUMENTS 8,214,098 B2 7/2012 Murray et al.
10,168,700 B2 1/2019 Gordon et al.
(Continued)

FOREIGN PATENT DOCUMENTS

WO 2020110378 A1 6/2020

OTHER PUBLICATIONS

Brewster, Thomas, "Drones With Facial Recognition Are Primed To Fly—But The World Isn't Ready Yet," retrieved on Dec. 8, 2021 from https://www.forbes.com/sites/thomasbrewster/2021/02/15/drones-with-facial-recognition-are-primed-to-fly-but-the-world-isnt-ready-yet/?sh=6af5447c3d9e, Forbes, Feb. 15, 2021, 6 pgs.
(Continued)

*Primary Examiner* — Ramsey Refai
(74) *Attorney, Agent, or Firm* — Perkins Coie LLP

(57) ABSTRACT

A technique is directed to methods and systems for providing drone-based assistance to a user. Drones may be utilized to aid users in performing tasks, such as assisting a user during an activity. The assistance can include providing a cooling flow of air, spraying a cooling mist of liquid, playing music, providing guidance, providing instructions, communicating with a device(s) to seek medical aid, retrieving sporting equipment, collecting performance metrics, collecting health metrics, or any assistance action. A user can connect to the drone via a device or using a set of built-in algorithms that employ biometric recognition to identify the user. Once activated and linked to the user, the drone can take flight. The drone can fly above, in front, or behind the user at a predetermined or adjustable height and provide airflow or mist from the drone blades to cool the user.

20 Claims, 6 Drawing Sheets

(51) Int. Cl.
 *G16H 40/63* (2018.01)
 *B64U 101/00* (2023.01)

(56) References Cited

U.S. PATENT DOCUMENTS

| | | | |
|---|---|---|---|
| 10,507,917 | B2 | 12/2019 | Taylor et al. |
| 10,597,155 | B2* | 3/2020 | Karabed ............... B64U 20/70 |
| 10,832,333 | B1* | 11/2020 | Spader ............... G06F 18/2413 |
| 10,907,940 | B1* | 2/2021 | Parker ................... G06N 20/00 |
| 10,980,218 | B2* | 4/2021 | Gorski ................... G16H 50/20 |
| 11,263,461 | B2* | 3/2022 | Marty .................... H04N 23/63 |
| 2010/0134614 | A1* | 6/2010 | Aman ............... A63B 24/0003 348/157 |
| 2012/0175468 | A1 | 7/2012 | Zerof |
| 2013/0253733 | A1* | 9/2013 | Lee ........................ G07C 5/008 701/2 |
| 2015/0002391 | A1* | 1/2015 | Chen ..................... H04N 23/56 345/156 |
| 2015/0157272 | A1* | 6/2015 | Balakrishnan ....... A61B 5/0002 600/595 |
| 2016/0378109 | A1* | 12/2016 | Raffa ..................... H04N 7/185 701/2 |
| 2017/0053169 | A1* | 2/2017 | Cuban ................... H04N 7/181 |
| 2017/0101178 | A1 | 4/2017 | Lee et al. |
| 2017/0160751 | A1* | 6/2017 | Pierce ................... B64C 39/024 |
| 2017/0231213 | A1 | 8/2017 | Gordon et al. |
| 2017/0235308 | A1* | 8/2017 | Gordon ................ G05D 1/0016 701/2 |
| 2017/0248970 | A1* | 8/2017 | Karabed ............... F04D 25/088 |
| 2017/0322628 | A1 | 11/2017 | Tan et al. |
| 2018/0025268 | A1* | 1/2018 | Teig ....................... G06N 3/063 706/25 |
| 2019/0389577 | A1 | 12/2019 | Jones et al. |
| 2021/0015079 | A1* | 1/2021 | Gorski ................... G16H 40/67 |
| 2021/0034843 | A1 | 2/2021 | Sivan et al. |
| 2021/0163136 | A1 | 6/2021 | Wake et al. |
| 2021/0299311 | A1 | 9/2021 | Yu |
| 2021/0300549 | A1 | 9/2021 | Beloussov et al. |

OTHER PUBLICATIONS

Debusmann Jr., Bernd, "Fitness drones are coming, if inventors can get all the kinks out of them," retrieved on Dec. 8, 2021 from https://www.washingtonpost.com/science/drones-for-exercising/2021/04/16/c459c7fe-882d-11eb-82bc-e58213caa38e_story.html, The Washington Post, Apr. 18, 2021, 3 pgs.

Corrigan, Fintan, "12 Best Follow Me Drones And Follow You Technology Reviewed," retrieved on Dec. 8, 2021 from https://www.dronezon.com/drone-reviews/best-follow-me-gps-mode-drone-technology-reviewed/, Dronezon, Oct. 18, 2020, 44 pages.

Hemsworth, Michael, "The 'AirBuddy' Conceptual Drone Offers Athletic Insight," retrieved on Dec. 8, 2021 from https://www.trendhunter.com/trends/conceptual-drone, TRENDHUNTER, Jun. 10, 2021, 6 pgs.

Chaari et al., "Development of Air Conditioner Robot Prototype That Follows Humans in Outdoor Applications," retrieved from https://www.mdpi.com/2079-9292/10/14/1700/htm, MDPI electronics, Jul. 15, 2021, 29 pgs.

* cited by examiner

METHODS AND SYSTEMS FOR DRONE BASED ASSISTANCE

BACKGROUND

When participating in outdoor activities, high temperatures make it difficult for an athlete to participate in the activities for long periods of time. Currently, athletes must take breaks to keep their bodies from overheating when participating in outdoor activities.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

DETAILED DESCRIPTION

Aspects of the present disclosure are directed to methods and systems for providing drone-based assistance to a user. Drones may be utilized to aid users in performing tasks, such as assisting a user during an activity (e.g., exercising, hiking, running, etc.). The assistance can include providing a cooling flow of air, spraying a cooling mist of liquid, playing music, providing guidance, providing instructions, communicating with a device(s) to seek medical aid, retrieving sporting equipment, collecting performance metrics, collecting health metrics, or any assistance action. For example, a drone hovers above a runner and provides a cooling flow of air from its blades upon the runner, as the runner participates in a running activity.

The drone can be equipped with attachments, such as sensing devices (e.g., 2D or 3D cameras, infrared cameras, night vision cameras, range finders, geolocation, motion sensors, temperature sensors, etc.), which capture data (e.g., flight instrumentation data, sensor data, image data, video data, weather data, user health data, geolocation data, performance data, etc.) about the user and the flight of the drone. The drone with the attachment(s) can perform the function of cooling and assisting the user during an activity. A user can connect to the drone via a device or using a set of built-in algorithms that employ biometric recognition to identify the user. Once activated and linked to the user, the drone can take flight. The drone can fly above, in front, or behind the user at a predetermined or adjustable height and provide airflow or mist from the drone blades to cool the user. The user can use a series of hand motions to indicate to the drone what type or amount of cooling to provide. The drone can also monitor the condition of the user and communicate for help if the user is injured.

Figure 1:
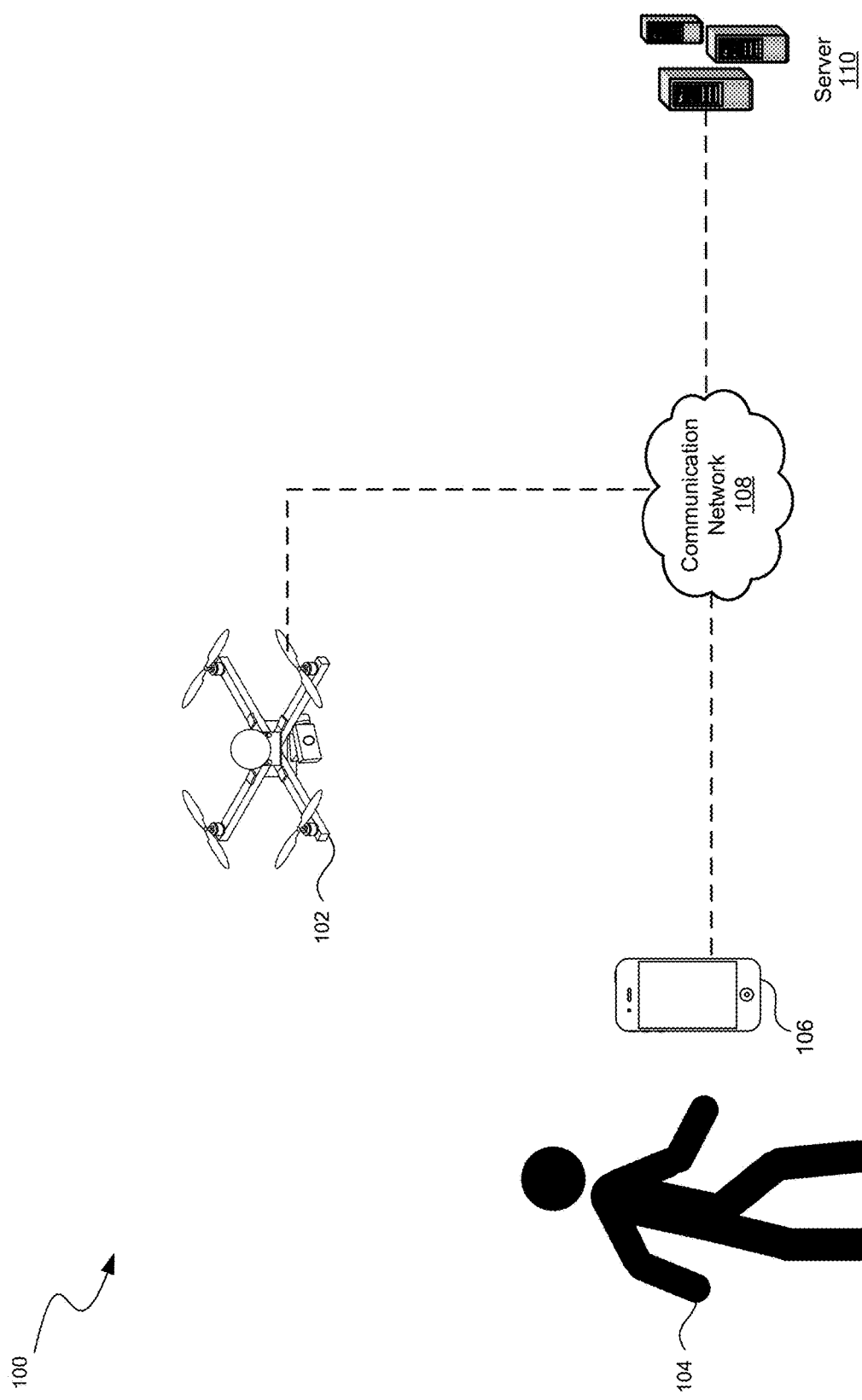
FIG. 1 is a schematic diagram showing a logical system architecture, in accordance with an embodiment.

Several implementations are discussed below in more detail in reference to the figures. In FIG. 1, a schematic diagram illustrates a logical system architecture 100. A user 104 (e.g., a subscriber, consumer, etc.) may use a mobile device 106 (e.g., smartphone, smartwatch, laptop, tablet, etc.) to communicate with drone 102 through communication network 108 (e.g., satellite network, cellular network, near-field communication (NFC) network, etc.). Drone 102 may be associated with a fleet of drones which are available to be requested for services from an airborne or grounded location. In an embodiment, the drone 102 is a personal drone and owned by user 104. In another embodiment, drone 102 may fly designated flight patterns (e.g., 3-dimensional flight patterns in geofencing perimeters) until a task is assigned. In another embodiment, drone 102 may hover above locations where tasks are frequently performed.

In an embodiment, user 104 may summon the drone 102 to perform a task (e.g., assisting user 104 by spraying cooling air or liquid on the user 104) with a gesture, such as a hand movement. In another embodiment, user 104 using mobile device 106 may request, from server 110, a drone to perform a task. In some implementations, once the user 104 summons or requests drone 102 for a service, an NFC network may be setup for the nearby devices (phones, smartwatch, cars, etc.) to connect to the drone 102. Server 110 may request access credentials associated with user 104 to authorize a drone to perform the task. The access credentials may verify user 104 is a subscriber and authorized to have a drone assist them. Server 110 may assign drone 102 to perform the task associated with user 104. In some cases, mobile device 106 may send a location for the task to occur to server 110. User 104 may receive a confirmation that the drone 102 has been assigned. In an embodiment, the drone 102 may navigate to the location and perform the task. User 104 can provide the drone 102 with instructions on the type of task and assistance.

Figure 2:
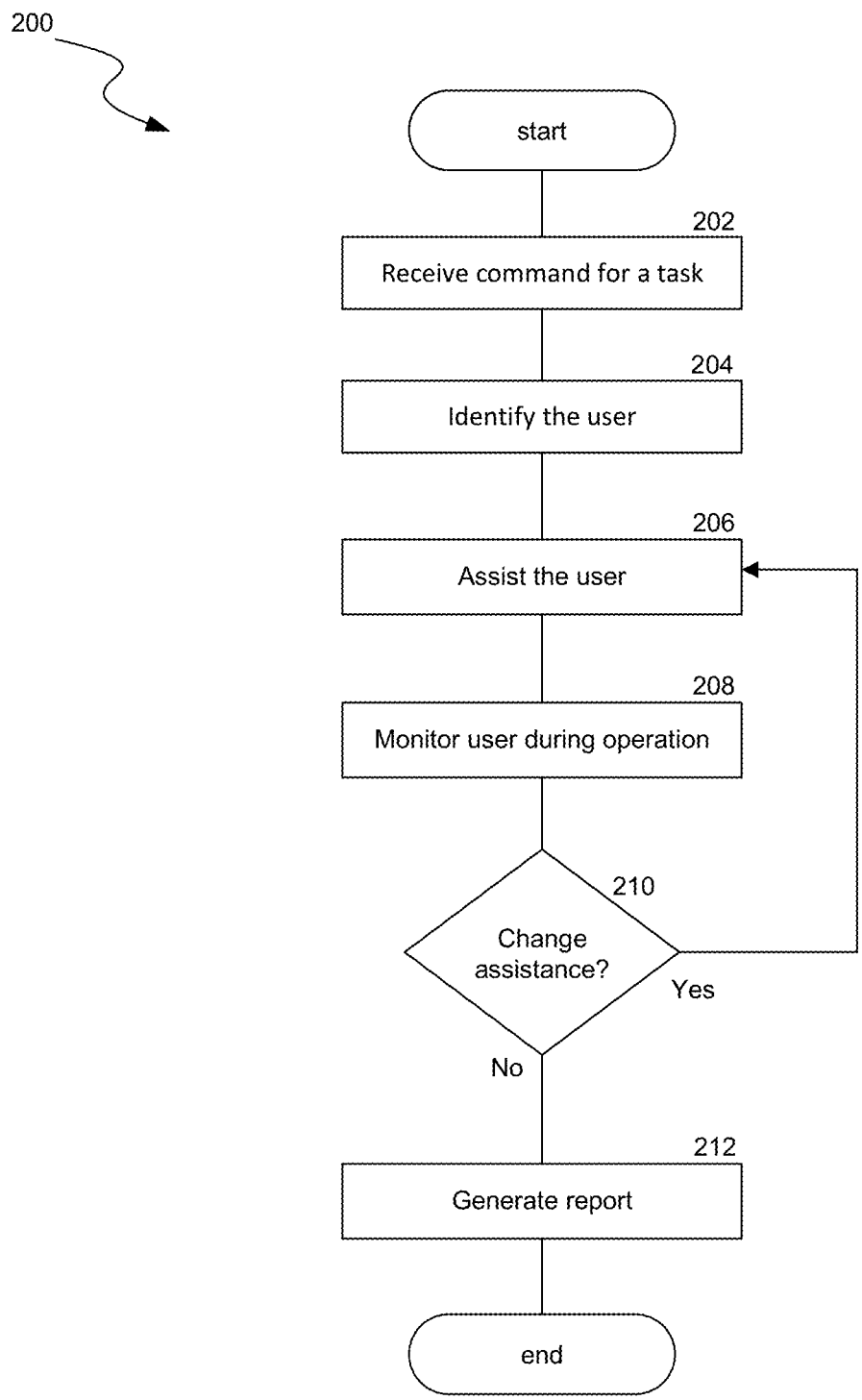
FIG. 2 is a flow diagram illustrating a process used in some implementations for providing drone-based assistance to a user.

FIG. 2 is a flow diagram illustrating a process 200 used in some implementations for providing drone-based assistance to a user. In some implementations, process 200 is triggered by a user requesting assistance by a drone, a drone powering on, a user communicating with a drone via a device, a device or drone connecting to a communication network, a user activating a subscription for drone assistance, powering on a device, a device or drone connecting to a gateway (e.g., router), a drone detecting a user activity, or the user downloading an assistance application on a device. In various implementations, process 200 is performed locally on the user device (or drone) or performed by cloud-based device(s) that can support a drone assisting a user for an activity.

At step 202, process 200 receives a command to perform a task for a user. The task can include assisting the user for an activity. The command can be pre-configured and sent from a device to the drone. In an example, the task is assisting the user during an exercise activity, such as a run or hike. A user can upload instructions to the drone. The instructions can include trail maps, biometrics (e.g., facial features, body features, etc.) of the recipient(s) of the assistance, health metrics (e.g., heart rate, BMI, blood pressure, weight, etc.) of the recipient(s) of the assistance, workout routines, length of activities, predefined cooling instructions, threshold distance (e.g., any threshold distance such as, 2 ft, 5 ft, 10 ft, etc.) from which to provide the assistance, objects (e.g., sporting equipment) to retrieve, devices to communicate with, or devices to receive captured data. In some implementations, the command is body gesture, such as a hand movement, detected by the drone or is a communication from a device.

At step 204, process 200 identifies the user to assist for the activity. Process 300 can identify the user based on biometric data (e.g., facial recognition, vocal patterns, or other demographics) or a user device.

Figure 3:
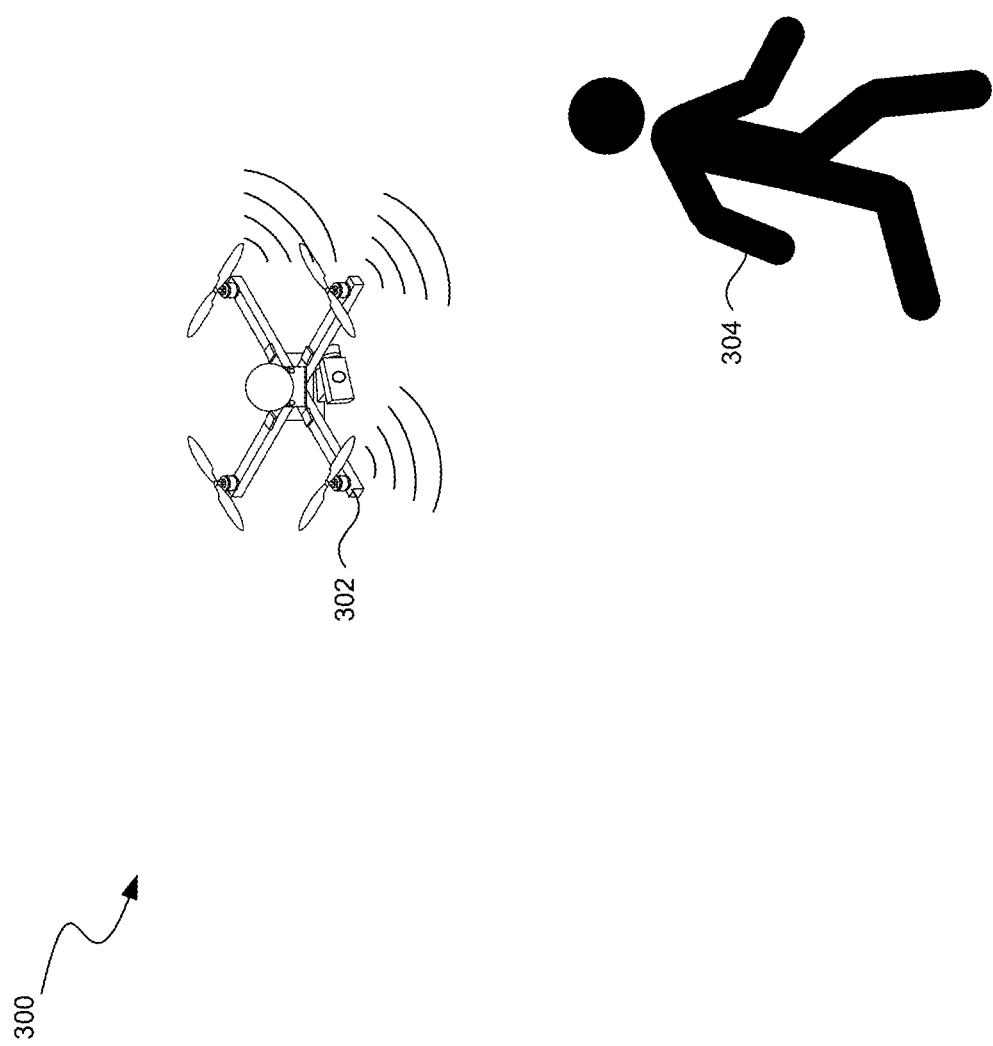
FIG. 3 is an illustration of drone-based assistance to a user.

At step 206, process 200 performs the task of assisting the user. The drone can operate at a threshold distance from the user while assisting the user. The drone can fly above, in front, or behind the user at a predetermined or adjustable height and assist the user. The user can use a series of hand motions to indicate to the drone what type or amount of assistance to provide. The assistance can include providing a cooling flow of air, spraying a cooling mist of liquid, playing audio content (e.g., music, podcast, broadcast, etc.), providing guidance (e.g., geolocation directions, coaching advise, etc.), providing instructions, communicating with a device(s) to seek medical aid, retrieving sporting equipment (e.g., ball, cone, racket, etc.), collecting performance metrics, collecting health metrics, receiving/reading/sending messages (e.g., emails, SMS, voicemails, etc.) or any assistance action. Example 300 of FIG. 3 illustrates a drone 302 assisting user 304 by providing cooling air from the blades of drone 302.

At step 208, process 200 monitors the user during operation to detect gestures or any form of communication and capture data, such as videos, images, or metrics, of the user during the activity. The drone can monitor the user to identify the user direction and orientation. Based on the user gestures, user commands (verbal or digital), user direction, or user orientation, the drone can adjust flight speed, height, or the type of assistance to provide to the user. For example, using the orientation and speed of the user, the drone determines the position (e.g., in front, above, or behind) and height from which to provide the assistance to the user. Process 200 can track a travel direction (e.g., one or more characteristics indicating a direction of travel, such as velocity, direction of gaze, pathway/roadway, etc.) to anticipate and/or adjust for turns the user might make while running. Based on the monitored travel direction, the drone can provide constant or intermittent assistance to the user during the activity. In some implementations, the drone can detect weather conditions, such as wind, and identify a position and distance from the user from which to provide the cooling air/liquid based on the weather conditions. The drone can account for an offset due to wind sheer/direction, such that delivery of a air/mist to a user would require the drone to fly in an offset position (i.e., not directly overhead of the user).

The drone can capture performance metrics (e.g., running pace, position in a competition, rank, distance traveled, etc.) and/or health metrics (e.g., heart rate, body temperature, breathing rate, etc.). In some implementations, the drone retrieves the metrics from a user wearable device or captures the metrics with attachments (e.g., sensors, cameras, laser thermometers, etc.). The drone can provide audible notifications to the user based on the captured data. For example, the drone can provide the user with a pace to catch a runner ahead of the user, provide the user with the distance to the next check point, provide the user with their performance or health metrics, provide the current rank in a competition, or provide the user with directions on where to turn. In another example, the drone can play music for the user to help the user maintain or increase an activity pace. In another example, the drone can provide an audible sound (e.g., tone, beep, song, chime, etc.) to indicate the user has traveled a distance (e.g., any distance such as 0.5-mile, 1 mile, 5 miles, etc.). The drone can also monitor the condition of the user and communicate for help (e.g., message a device, call 911, etc.) if the user's health metrics are outside of health range.

In some implementations, the drone determines to assist the user based on the captured performance or health metrics. For example, if the user's health metrics are outside of health range the drone begins cooling the user with air or liquid. In some implementations, the user can command the drone to assist other users.

In some implementations, based on the user's biometrics, performance metrics, and/or health metrics, the drone can dynamically determine and/or alter assistance or guidance to the user, to give the user a workout. In a first example, if the drone detects that the user is tired, based on the performance metrics (e.g., decreasing pace, shorter strides, etc.) or health metrics (e.g., elevated breathing rate, increasing heart rate, etc.), the drone can use the geographical data to select a shorter path for the activity or path with less changes in elevation. In a second example, if the user is not meeting their stated workout parameters, the drone selects a path that provides a more arduous workout, such as changes in elevation or an increased pace.

At step 210, process 200 determines whether to change the assistance to the user. The drone can modify the assistance to the user based on a gesture (e.g., a hand movement), or communication (e.g., verbal, or digital) from the user. The drone can identify gestures of the user and alter the type of assistance. For example, a first gesture (e.g., left hand waiving) indicates the user is requesting cooling air, a second gesture (e.g., right hand waiving) indicates the user is requesting cooling liquid, a third gesture (e.g., user holds arm above their head) indicates to the drone to stop providing cooling air or liquid, a fourth gesture (e.g., fast hand waiving) indicates the user wants more cooling air or liquid, a fifth gesture (e.g., slow hand waiving) indicates the user wants less cooling air or liquid, a sixth gesture (e.g., arrangement of fingers on the user's hand) indicates for the drone to move further away from the user, or a seventh gesture (e.g., arrangement of fingers on the user's hand) indicates for the drone to come closer to the user. In some implementations, the user can provide verbal commands to the microphone on the drone to indicate the type and amount of assistance to provide. The drone can communicate with other drones to coordinate assistance to the user. For example, if the battery level of the drone or the cooling liquid level in a drone tank is below a threshold, the drone communicates with another drone to take over and assist the user during the activity.

At step 212, process 200 generates and sends a report of the captured data to a device(s). For example, the drone can send the captured data (e.g., images, videos, performance metrics, health metrics, etc.) to coaches or family members of the user during the activity. The drone can upload captured data of the activity to cloud-based or local storage. In some cases, the drone can stream the captured data to devices.

Figure 4:
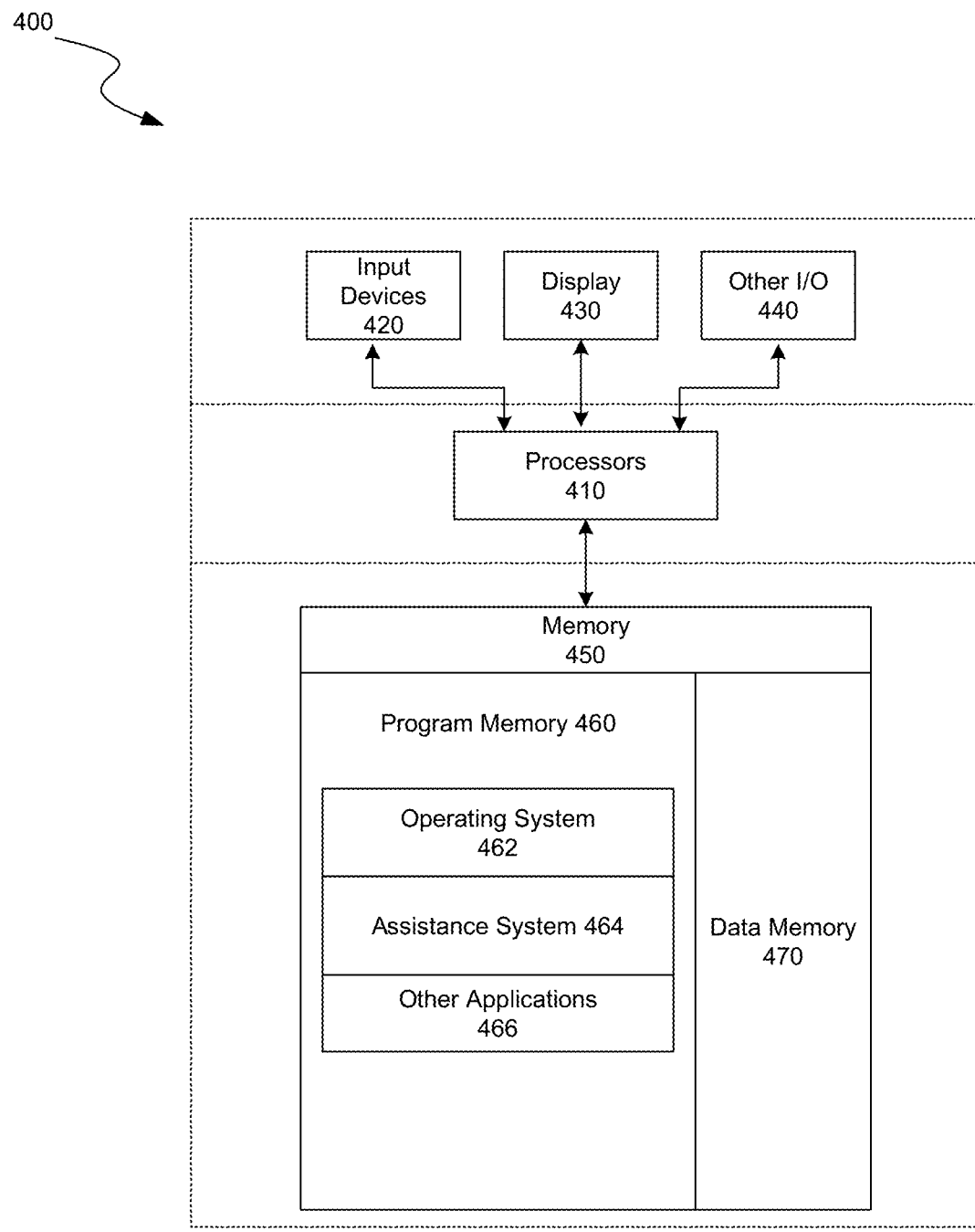
FIG. 4 is a block diagram illustrating an overview of devices on which some implementations can operate.

FIG. 4 is a block diagram illustrating an overview of devices on which some implementations of the disclosed technology can operate. The devices can comprise hardware components of a device 400 that manage entitlements within a real-time telemetry system. Device 400 can include one or more input devices 420 that provide input to the processor(s) 410 (e.g., CPU(s), GPU(s), HPU(s), etc.), notifying it of actions. The actions can be mediated by a hardware controller that interprets the signals received from the input device and communicates the information to the processors 410 using a communication protocol. Input devices 420 include, for example, a mouse, a keyboard, a touchscreen, an infrared sensor, a touchpad, a wearable input device, a camera- or image-based input device, a microphone, drone, or other user input devices.

Processors 410 can be a single processing unit or multiple processing units in a device or distributed across multiple devices. Processors 410 can be coupled to other hardware devices, for example, with the use of a bus, such as a PCI bus or SCSI bus. The processors 410 can communicate with a hardware controller for devices, such as for a display 430. Display 430 can be used to display text and graphics. In some implementations, display 430 provides graphical and textual visual feedback to a user. In some implementations, display 430 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 440 can also be coupled to the processor, such as a network card, video card, audio card, USB, firewire or other external device, camera, printer, speakers, CD-ROM drive, DVD drive, disk drive, or Blu-Ray device.

In some implementations, the device 400 also includes a communication device capable of communicating wirelessly or wire-based with a network node. The communication device can communicate with another device or a server through a network using, for example, TCP/IP protocols. Device 400 can utilize the communication device to distribute operations across multiple network devices.

The processors 410 can have access to a memory 450 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 450 can include program memory 460 that stores programs and software, such as an operating system 462, assistance system 464, and other application programs 466. Memory 450 can also include data memory 470, user interface data, activity data, image data, biometric data, sensor data, device data, location data, network learning data, machine learning data, application data, alert data, structure data, user data, instruction data, camera data, retrieval data, management data, notification data, configuration data, settings, user options or preferences, etc., which can be provided to the program memory 460 or any element of the device 400.

Some implementations can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 5:
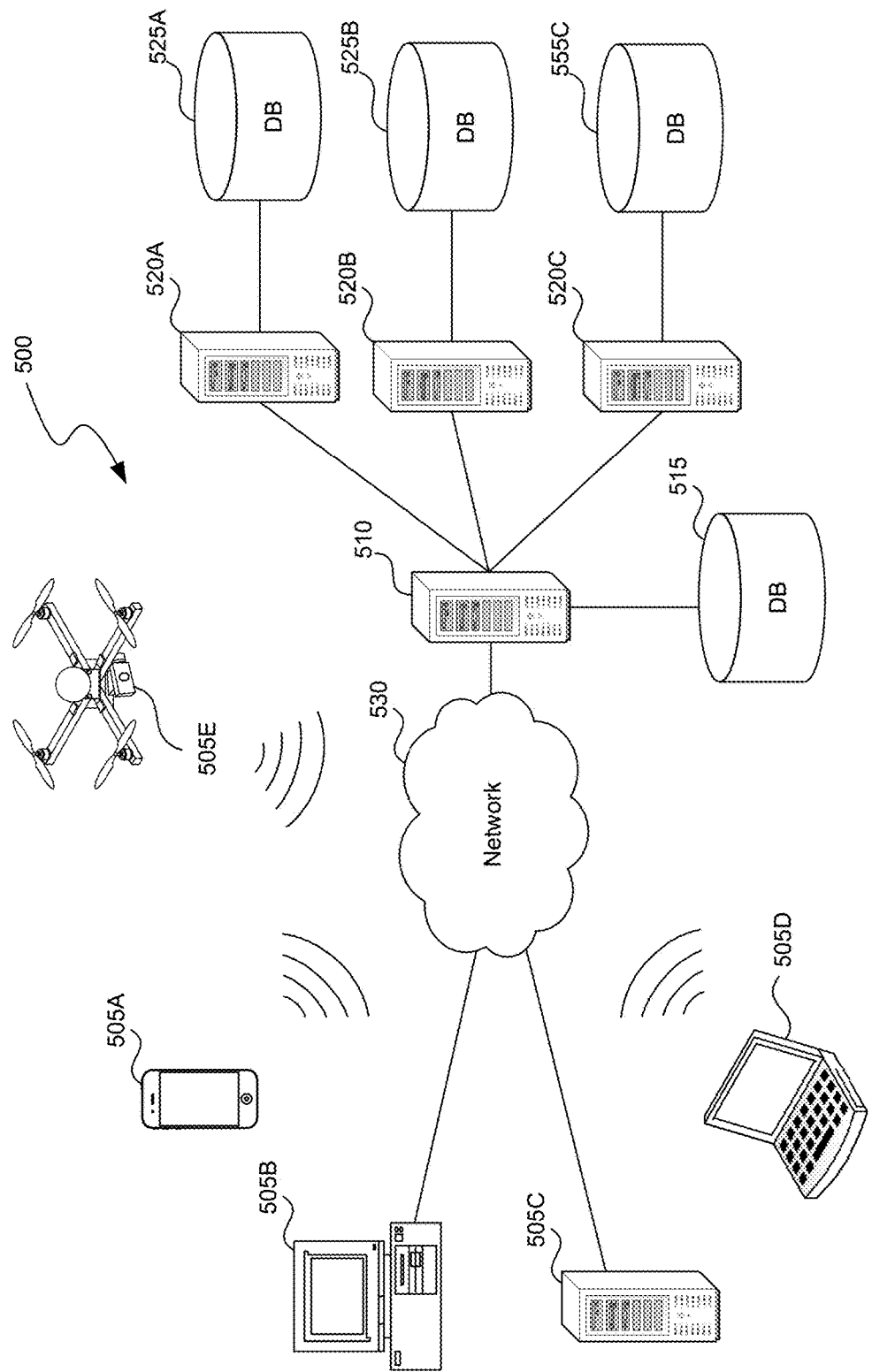
FIG. 5 is a block diagram illustrating an overview of an environment in which some implementations can operate.

FIG. 5 is a block diagram illustrating an overview of an environment 500 in which some implementations of the disclosed technology can operate. Environment 500 can include one or more client computing devices 505A-E, examples of which can include device 400. Client computing devices 505 can operate in a networked environment using logical connections through network 530 to one or more remote computers, such as a server computing device 510.

In some implementations, server 510 can be an edge server which receives client requests and coordinates fulfillment of those requests through other servers, such as servers 520A-C. Server computing devices 510 and 520 can comprise computing systems, such as device 400. Though each server computing device 510 and 520 is displayed logically as a single server, server computing devices can each be a distributed computing environment encompassing multiple computing devices located at the same or at geographically disparate physical locations. In some implementations, each server 520 corresponds to a group of servers.

Client computing devices 505 and server computing devices 510 and 520 can each act as a server or client to other server/client devices. Server 510 can connect to a database 515. Servers 520A-C can each connect to a corresponding database 525A-C. As discussed above, each server 520 can correspond to a group of servers, and each of these servers can share a database or can have their own database. Databases 515 and 525 can warehouse (e.g., store) information such as implement data, user interface data, activity data, image data, biometric data, sensor data, device data, drone data, task data, location data, network learning data, machine learning data, application data, alert data, structure data, user data, instruction data, camera data, retrieval data, management data, notification data, and configuration data. Though databases 515 and 525 are displayed logically as single units, databases 515 and 525 can each be a distributed computing environment encompassing multiple computing devices, can be located within their corresponding server, or can be located at the same or at geographically disparate physical locations.

Network 530 can be a local area network (LAN) or a wide area network (WAN) but can also be other wired or wireless networks. Network 530 may be the Internet or some other public or private network. Client computing devices 505 can be connected to network 530 through a network interface, such as by wired or wireless communication. While the connections between server 510 and servers 520 are shown as separate connections, these connections can be any kind of local, wide area, wired, or wireless network, including network 530 or a separate public or private network.

Figure 6:
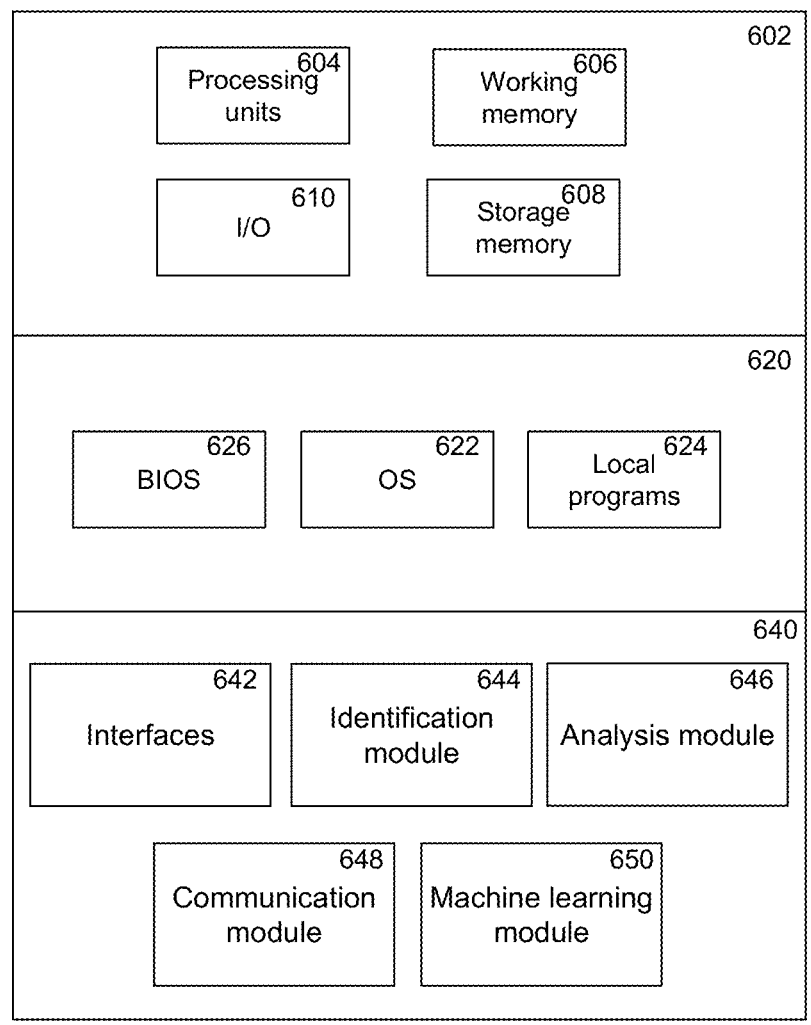
FIG. 6 is a block diagram illustrating components which in some implementations can be used in a system employing the disclosed technology.

FIG. 6 is a block diagram illustrating components 600 which, in some implementations, can be used in a system employing the disclosed technology. The components 600 include hardware 602, general software 620, and specialized components 640. As discussed above, a system implementing the disclosed technology can use various hardware including processing units 604 (e.g., CPUs, GPUs, APUs, etc.), working memory 606, storage memory 608 (local storage or as an interface to remote storage, such as storage 515 or 525), and input and output devices 610. In various implementations, storage memory 608 can be one or more of: local devices, interfaces to remote storage devices, or combinations thereof. For example, storage memory 608 can be a set of one or more hard drives (e.g., a redundant array of independent disks (RAID)) accessible through a system bus or can be a cloud storage provider or other network storage accessible via one or more communications networks (e.g., a network accessible storage (NAS) device, such as storage 615 or storage provided through another server 520). Components 600 can be implemented in a client computing device such as client computing devices 505 or on a server computing device, such as server computing device 510 or 520.

General software 620 can include various applications including an operating system 622, local programs 624, and a basic input output system (BIOS) 626. Specialized components 640 can be subcomponents of a general software application 620, such as local programs 624. Specialized components 640 can include identification module 644, analysis module 646, communication module 648, machine learning module 650, and components which can be used for providing user interfaces, transferring data, and controlling the specialized components, such as interfaces 642. In some implementations, components 600 can be in a computing system that is distributed across multiple computing devices or can be an interface to a server-based application executing one or more of specialized components 640. Although depicted as separate components, specialized components 640 may be logical or other nonphysical differentiations of functions and/or may be submodules or code-blocks of one or more applications.

In some embodiments, the identification module 644 is configured to identify the activity, the type of assistance to provide to the user. A drone can use the identification module 644 to determine the user, task, activity, or type of assistance based on a device command, biometric sensors (e.g., facial recognition, vocal patterns, or other demographics), cameras (e.g., infrared, heat detection, etc.), or microphones. A drone can use the identification module 644 to identify user gestures, user direction, and orientation. Based on the user gestures, user direction, and orientation, the drone can adjust flight speed, height, or the type of assistance to provide to the user.

In some embodiments, the analysis module 646 is configured to analyze user activities, tasks, gestures, or device commands to determine how to assist a user. The analysis module 646 analyses a user activity and determine to provide cooling air/liquid to the user. Based on the geolocation and speed of the user, the drone may use the analysis module 646 to determine position and orientation (e.g., in front, above, or behind) from which to provide the assistance to the user.

Communications module 648 is associated with sending/receiving information (e.g., user/task/activity information from identification module 644, analysis module 646, and machine learning module 650) with a remote server or with one or more client devices, drones, streaming devices, OTA boxes, set-top boxes, etc. These communications can employ any suitable type of technology, such as Bluetooth, WiFi, WiMax, cellular, single hop communication, multi-hop communication, Dedicated Short Range Communications (DSRC), or a proprietary communication protocol. In some embodiments, communications module 648 sends information identified by the identification module 644 and information analyzed by the analysis module 646. Furthermore, communications module 648 may be configured to communicate data with a client device and/or OTA box, smart OTA antenna, etc. to determine how to assist a user in an activity.

Machine learning module 650 may be configured to analyze user history of activities to identify the activity of the user and determine the type of assistance (e.g., providing cooling air/liquid, instructions, etc.) to provide to the user. The machine learning module 650 may be configured to identify the activity based on at least one machine-learning algorithm trained on at least one dataset reflecting a user's activities and type of requested assistance. The at least one machine-learning algorithms (and models) may be stored locally at databases and/or externally at databases (e.g., cloud databases and/or cloud servers). Client devices may be equipped to access these machine learning algorithms and intelligently identify user activities based on at least one machine-learning model that is trained on a user's historical activity history. For example, if a user frequently runs marathons or runs recreationally, the user's viewing history may be collected to train a machine-learning model to then automatically identify running activities based on the user's movements. In other example aspects, a user may demonstrate a preference for certain types of assistance based on the activity, such as cooling air for running competitions (e.g., marathon event) but playing music for recreational running events (e.g., personal morning run).

As described herein, a machine-learning (ML) model may refer to a predictive or statistical utility or program that may be used to determine a probability distribution over one or more character sequences, classes, objects, result sets or events, and/or to predict a response value from one or more predictors. A model may be based on, or incorporate, one or more rule sets, machine learning, a neural network, or the like. In examples, the ML models may be located on the client device, service device, a network appliance (e.g., a firewall, a router, etc.), or some combination thereof. The ML models may process user activity history and other data stores of user activities (e.g., social media profiles) to determine which activities should be automatically stored. Determining whether a certain activity should be identified and stored may comprise identifying various characteristics of a user's activity history and preferences. For instance, if a user has a social media profile that displays several photographs of the user engaging in sporting activities, then the assistance system described herein may determine that certain sporting activities should be identified as potential user activities that may require drone assistance. Similarly, if a user posts certain social media items reflecting a favorite activity, the assistance system may determine that the favorite activity should be identified. Based on an aggregation of data from a user's activity history, social media profiles, and other user data stores, at least one ML model may be trained and subsequently deployed to automatically identify and/or assist a user during the activity. The trained ML model may be deployed to one or more devices. As a specific example, an instance of a trained ML model may be deployed to a server device and to a client device. The ML model deployed to a server device may be configured to be used by the client device when, for example, the client device is connected to the Internet. Conversely, the ML model deployed to a client device may be configured to be used by the client device when, for example, the client device is not connected to the Internet. In some instances, a client device may not be connected to the Internet but still configured to receive satellite signals with activity/task information. In such examples, the ML model may be locally cached by the client device.

Those skilled in the art will appreciate that the components illustrated in FIGS. 4-6 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Reference in this specification to "implementations" (e.g. "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle-specified number of items, or that an item under comparison has a value within a middle-specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

Unless explicitly excluded, the use of the singular to describe a component, structure, or operation does not exclude the use of plural such components, structures, or operations. As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

As used herein, the expression "at least one of A, B, and C" is intended to cover all permutations of A, B and C. For example, that expression covers the presentation of at least one A, the presentation of at least one B, the presentation of at least one C, the presentation of at least one A and at least one B, the presentation of at least one A and at least one C, the presentation of at least one B and at least one C, and the presentation of at least one A and at least one B and at least one C.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

I claim:

1. A method comprising:
receiving, by at least one drone, a command to perform at least one task for a user,
   wherein the at least one task includes providing, by the at least one drone, assistance to the user for an activity;
identifying, based on biometric data, the user to receive the assistance for the activity;
determining one or more weather conditions of an environment of the activity;
determining an operational distance from the user for the at least one drone to provide the assistance to the user based on the one or more weather conditions;
operating the at least one drone at the operational distance from the user while providing the assistance to the user;
in response to monitoring the user during the activity, detecting at least one gesture of the user; and
modifying the at least one task based on the at least one gesture.

2. The method of claim 1, further comprising:
identifying a type of activity of the user; and
determining a type of assistance to provide based on the type of activity.

3. The method of claim 1, further comprising:
collecting at least one performance metric of the user during the activity; and
generating a report based on the at least one performance metric of the user during the activity.

4. The method of claim 1, further comprising:
outputting an alert to the user to indicate instructions regarding the activity.

5. The method of claim 1, further comprising:
collecting at least one health metric of the user during the activity; and
modifying the at least one task based on the at least one health metric.

6. The method of claim 1, wherein the activity is identified by at least one machine-learning algorithm, wherein the at least one machine-learning algorithm is trained based on at least one dataset associated with a past activity history.

7. The method of claim 1,
wherein the activity is an exercising activity, and wherein the assistance is providing a flow of cooling air or liquid to the user.

8. A computing system comprising:

at least one processor; and at least one memory storing instructions that, when executed by the at least one processor, cause the computing system to perform a process comprising:

receiving, by at least one drone, a command to perform at least one task for a user,
wherein the at least one task includes providing, by the at least one drone, assistance to the user for an activity;
identifying, based on biometric data, the user to receive the assistance for the activity;
determining one or more weather conditions of an environment of the activity;
determining an operational distance from the user for the at least one drone to provide the assistance to the user based on the one or more weather conditions;
operating the at least one drone at the operational distance from the user while providing the assistance to the user;
in response to monitoring the user during the activity, detecting at least one gesture of the user; and
modifying the at least one task based on the at least one gesture.

9. The computing system of claim 8, wherein the process further comprises:

identifying a type of activity of the user; and determining a type of assistance to provide based on the type of activity.

10. The computing system of claim 8, wherein the process further comprises:

collecting at least one performance metric of the user during the activity; and generating a report based on the at least one performance metric of the user during the activity.

11. The computing system of claim 8, wherein the process further comprises:

outputting an alert to the user to indicate instructions regarding the activity.

12. The computing system of claim 8, wherein the process further comprises:

collecting at least one health metric of the user during the activity; and modifying the at least one task based on the at least one health metric.

13. The computing system of claim 8, wherein the activity is identified by at least one machine-learning algorithm, wherein the at least one machine-learning algorithm is trained based on at least one dataset associated with a past activity history.

14. The computing system of claim 8, wherein the activity is an exercising activity, and wherein the assistance is providing a flow of cooling air or liquid to the user.

15. A non-transitory computer-readable medium storing instructions that, when executed by a computing system, cause the computing system to perform operations comprising:

receiving, by at least one drone, a command to perform at least one task for a user,
wherein the at least one task includes providing, by the at least one drone, assistance to the user for an activity;
identifying, based on biometric data, the user to receive the assistance for the activity;
determining one or more weather conditions of an environment of the activity;
determining an operational distance from the user for the at least one drone to provide the assistance to the user based on the one or more weather conditions;
operating the at least one drone at the operational distance from the user while providing the assistance to the user;
in response to monitoring the user during the activity, detecting at least one gesture of the user; and
modifying the at least one task based on the at least one gesture.

16. The non-transitory computer-readable medium of claim 15, wherein the operations further comprise:

identifying a type of activity of the user; and determining a type of assistance to provide based on the type of activity.

17. The non-transitory computer-readable medium of claim 15, wherein the operations further comprise:

collecting at least one performance metric of the user during the activity; and generating a report based on the at least one performance metric of the user during the activity.

18. The non-transitory computer-readable medium of claim 15, wherein the operations further comprise:

outputting an alert to the user to indicate instructions regarding the activity.

19. The non-transitory computer-readable medium of claim 15, wherein the operations further comprise:

collecting at least one health metric of the user during the activity; and modifying the at least one task based on the at least one health metric.

20. The non-transitory computer-readable medium of claim 15, wherein the activity is identified by at least one machine-learning algorithm, wherein the at least one machine-learning algorithm is trained based on at least one dataset associated with a past activity history, wherein the activity is an exercising activity, and wherein the assistance is providing a flow of cooling air or liquid to the user.

* * * * *